(12) United States Patent
Albadri et al.

(10) Patent No.: US 7,681,438 B2
(45) Date of Patent: Mar. 23, 2010

(54) APPARATUS AND METHOD FOR MEASUREMENT OF HARDENABLE MATERIAL CHARACTERISTICS

(75) Inventors: Ali Albadri, Sutton (GB); Andrew Smith, Horsham (GB); Paul Rogers, Waterlooville (GB); Peter Male, Stourbridge (GB)

(73) Assignee: Hydronix Limited, Guildford (GB)

( * ) Notice: Subject to any disclaimer, the term of this patent is extended or adjusted under 35 U.S.C. 154(b) by 350 days.

(21) Appl. No.: 11/683,341

(22) Filed: Mar. 7, 2007

(65) Prior Publication Data

US 2007/0210814 A1     Sep. 13, 2007

(30) Foreign Application Priority Data

Mar. 7, 2006    (EP) .................................. 06251199

(51) Int. Cl.
 *B23Q 17/20*    (2006.01)
(52) U.S. Cl. .......................................................... 73/78
(58) Field of Classification Search ...................... 73/78, 73/781; 324/643, 689; 374/55–56
See application file for complete search history.

(56) References Cited

U.S. PATENT DOCUMENTS

| 4,943,930 | A |   | 7/1990 | Radjy |
| 5,445,178 | A |   | 8/1995 | Feuer |
| 5,541,855 | A | * | 7/1996 | Enzler et al. ................. 702/113 |
| 5,939,889 | A | * | 8/1999 | Zoughi et al. ................ 324/643 |
| 6,023,170 | A |   | 2/2000 | Hilhorst et al. |
| 6,819,121 | B1 |  | 11/2004 | Hager, III et al. |
| 6,865,515 | B2 |  | 3/2005 | Fox et al. |
| 7,231,815 | B2 | * | 6/2007 | Kanare .......................... 73/73 |
| 7,581,446 | B2 | * | 9/2009 | Troxler ........................ 73/623 |
| 2003/0015024 | A1 | | 1/2003 | Campbell et al. |

FOREIGN PATENT DOCUMENTS

WO     WO 96/18084     6/1996

OTHER PUBLICATIONS

European Search Report; EP 06 25 1199; Mar. 8, 2007.

* cited by examiner

*Primary Examiner*—Hezron Williams
*Assistant Examiner*—Rodney T Frank
(74) *Attorney, Agent, or Firm*—Hogan & Hartson LLP (57) ABSTRACT

A probe for measuring the hardness of concrete includes a body adapted to receive a retainer such that the combined body and retainer can be held in an aperture extending through a wall of a mould for the hardenable material, with the body extending from the inside of the wall. A sensor circuit includes detector elements supported by the body and disposed when in use in the concrete, and circuit terminals which face the exterior of the mould wall when in use, and are accessible through the retainer for connection to terminals of an external instrument. Preferably, the detector elements are conductive portions of a printed circuit board forming a resonator. The instrument can operate a switch in the probe which interconnects the terminals to indicate a good connection and measures resonator impedance at multiple frequencies.

12 Claims, 8 Drawing Sheets

APPARATUS AND METHOD FOR MEASUREMENT OF HARDENABLE MATERIAL CHARACTERISTICS

RELATED APPLICATION

This application claims priority of European Patent Application No. EP 06251199.3 filed Mar. 7, 2006, entitled MEASUREMENT OF HARDENABLE MATERIAL CHARACTERISTICS, which is incorporated herein in its entirety by this reference.

FIELD OF THE INVENTION

This invention relates to a method and apparatus for detecting a characteristic of a hardenable material. The invention is particularly, but not exclusively, applicable to detecting the hardness of a cementitious material such as concrete, but is also applicable to detecting other characteristics of a range of construction materials.

BACKGROUND OF THE INVENTION

It is known to provide a probe for measuring characteristics of a hardenable construction material. For example, one known system for measuring the hardness of concrete (see U.S. Pat. No. 6,023,170) uses at least two electrodes which are placed in the concrete for the purpose of measuring the dielectric characteristics of the concrete, which are related to the hardness of the concrete.

Figure 1:
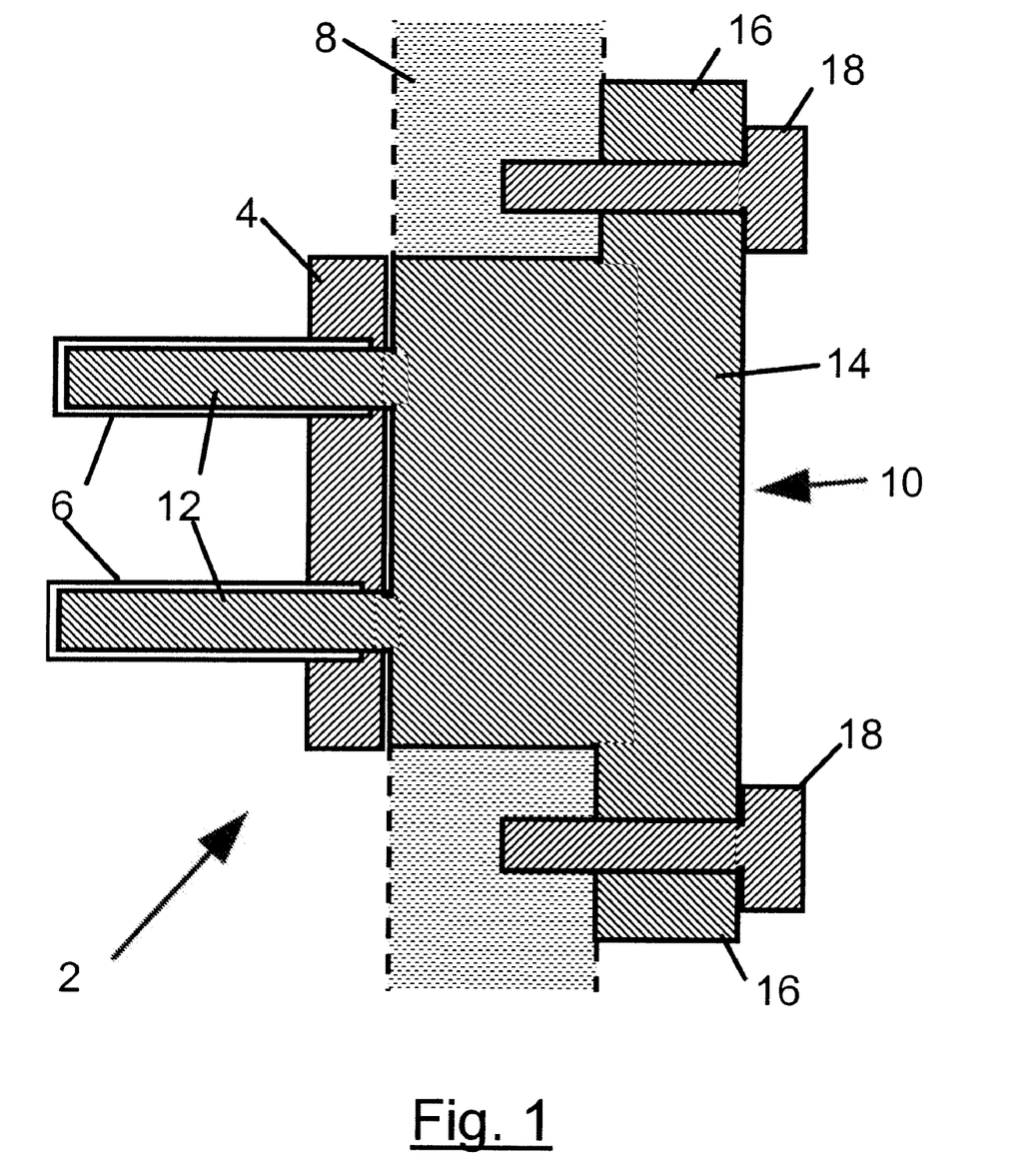
FIG. 1 is a schematic section view of a prior art probe for measuring the hardness of concrete.

It is known to provide a probe structure as shown in FIG. 1. The probe 2 comprises a base 4 and two hollow cylindrical metal tubes 6, and is supported in wooden formwork 8. The probe 4 is first attached to a holder 10 by sliding the cylindrical metal tubes 6 on to two prongs 12 of the holder 10. The probe 2 is then supported on the inside of the formwork 8 by disposing a central cylindrical section 14 of the holder within a hole drilled in the formwork 8. Flanges 16 of the holder 10 have holes extending therethrough to permit the holder 10 to be fastened to the formwork using screws 18. After the concrete has set, the holder 10 can be removed, thus permitting the terminals of a connector to be fitted into the cylindrical metal tubes 6, thereby enabling a measurement of dielectric characteristics of the concrete surrounding the tubes 6.

This arrangement suffers from a number of disadvantages. First, the dielectric measurements made using the probe 2 do not distinguish clearly between materials of different characteristics, particularly when the characteristics are similar. Second, the holder 10 can only be removed to permit connection of an instrument after the material within which the probe 2 is embedded has hardened. Accordingly, the probe cannot be used during the initial stages of hardening. A further disadvantage is that the construction of the holder 10 is such that it can only be used with wooden formwork or shuttering 8 in which the screws 18 can be fastened, and only with shuttering 8 of a limited range of thicknesses. Also, there is a significant chance of leakage of the hardening material through the hole drilled in the formwork 8, around the circumference of the holder 10.

It would be desirable to provide an arrangement which overcomes or mitigates at least some of these disadvantages. It would also be desirable to provide a measurement system which can be used throughout a very wide range of situations.

It would be desirable to provide a measurement probe which can be used for hardness testing within an experimental set-up, as well for "in-situ" strength measurements of concrete in a variety of different physical locations, which vary in their accessibility as well as in the size and shape of the concrete masses. It would also be desirable to achieve this while using a low-cost, consumable, embedded measurement probe.

SUMMARY OF THE INVENTION

Aspects of the present invention are set out in the accompanying claims.

The invention will be described primarily in the context of a probe for measuring the hardness of concrete which is poured into a mould defined by formwork, but the invention is equally applicable for measuring other characteristics and for use with other hardenable construction materials (such as gypsum).

According to a further aspect of the invention, a measurement probe for measuring a characteristic of hardenable construction material (e.g. for measuring characteristics indicative of the hardness of concrete) comprises a body supporting components of a sensor circuit. The body has means for attachment to a retainer so that the body can be held in position within a mass of hardenable material before the hardenable material has set. The attachment means is designed so as to permit access to terminals of the sensor circuit while the body is held in position by its attachment to the retainer. The attachment means of the body is preferably an inner cylindrical surface of a hollow portion of the body, the surface preferably being threaded. In this way, the outer cylindrical surface of the retainer can be fitted through a hole in a mould wall and attached within the body of the probe.

The retainer may engage the outer surface of a mould wall and the body engage the inner surface of the mould wall, to hold the probe and retainer in position. Such an arrangement allows for use of the probe in a variety of different situations. Different retainers can be used for different thicknesses of the mould wall.

Preferably, there is also or alternatively provided a retainer having a different configuration which is intended for permitting the probe to be mounted entirely from the exterior of the mould wall. The retainer is fitted to the probe, and is provided with an outer annular resilient ring member. The mould wall has a hole sized to permit the probe to be inserted through the wall. However, the resilient annular member has a portion which extends into the hole, between the wall of the hole and the retainer. After insertion of the probe through the hole in the mould wall, a tightening member is used to compress the ring between the tightening member and the probe. This expands the portion of the ring between the wall of the hole and the main body of the retainer so as to hold the retainer, and thus the probe, in position. The annular member may be used as seal, and can form a significantly more effective one than in the prior art arrangements. The member may also have a thicker portion forming a flange larger than the hole to assist in sealing the hole and/or locating the retainer in position.

Preferably, the tightening member is a cylindrical sleeve threadably mounted on the main body of the retainer. Preferably, interengaging threads on the probe body and the retainer are threaded in the opposite sense to the threads between the tightening member and the main body of the retainer, so that tightening of the tightening member does not transmit, via the resilient member, a force tending to unfasten the probe. Preferably the resilient member is engaged under a lip of the body of the probe, so as to prevent the retaining member from being displaced outwardly, over the end of the probe body.

A measuring instrument is preferably also provided, the instrument having terminals for connecting to the terminals of the sensor circuit carried by the measuring probe. Preferably, the probe and instrument have interengageable formations to ensure that the instrument and probe are in a predetermined relative orientation to facilitate interconnection of the terminals.

In the harsh surroundings often encountered when using construction materials, there is a danger that terminals of a probe may not make proper connections with terminals of an external instrument. This may be because deposits of hardenable material prevents proper fitting of the instrument to the probe, or because the material is deposited on the terminals themselves, preventing proper electrical connection. One possible solution to this problem would be to detect whether the measurement produced using the probe is indicative of a poor connection. However, it can be difficult to distinguish between such measurements and genuine measurements encountered in particular states of the hardenable material. This is especially the case when the measurement probe is designed to produce a wide variety of outputs depending upon the characteristics of the material, which is generally desirable to facilitate distinguishing between different conditions of the material.

According to a further aspect of the invention, the sensor circuit of a probe for measuring the characteristics of a hardenable material has terminals for connection to an external instrument. Two terminals of the sensor circuit are interconnected by a switch which can be operated by the external instrument when it is connected to the probe. In this way, the external instrument can detect that it is correctly coupled to the terminals of the sensor circuit. Preferably, the switch is operated by applying a signal to one of the terminals across which it is connected, although if desired a third terminal could be provided to carry a signal controlling the switch operation.

Preferably, the two terminals across which the switch is connected are also connected to a sensor device with characteristics dependent upon the characteristics of hardenable material in proximity to the sensor device. Preferably, the sensor device carries a high frequency signal which is influenced by the characteristics of the hardenable material. Preferably, at least one of the terminals is connected to the sensor device by a capacitor which conducts the high frequency signal, but which blocks a DC signal used to operate the switch. The switch may for example be a PIN diode which is closed in response to a DC current applied therethrough, and which has response characteristics such that it cannot be operated in response to the high frequency signal used to operate the sensor device.

In accordance with a further aspect of the invention, the sensor circuit of a probe for measuring the characteristics of a hardenable material comprises a resonator which, in use of the probe, is embedded in the hardenable material, and which is formed by conductive portions of a printed circuit board.

Although resonators have been used in the past for measuring characteristics of concrete being mixed in a mixer, the resonators have been bulky and expensive devices and therefore unsuitable for use as a consumable probe embedded in concrete. However, by forming the resonator out of the conductive portions of a printed circuit board, it has been found that a resonator of adequate characteristics can be made sufficiently inexpensively to make it commercially attractive to use as an embedded, consumable sensor probe. Appropriate operation of the resonator can produce material measurements which are significantly better, particularly in terms of the signal-to-noise ratio, than non-resonator embedded sensors.

The resonator characteristics can be enhanced by forming gaps in the printed circuit board within which, in use, the hardenable material is situated. For a given area of the conductive portions, the gaps produce a larger region over which the hardenable material is in intimate contact with the edges of the conductive portion. It is believed that this reduces the dependency of the sensor on the distribution of the components (e.g. the aggregate masses) of the surrounding material, and thus reduces the variability of the measurements. The gaps may be of any desired shape, such as circular, but better results are achieved if the gaps are in the form of elongate slots.

Preferably, the resonator is formed by conductive portions each disposed on a respective side of the printed circuit board.

In accordance with a still further aspect of the invention, there is provided a method of measuring characteristics of hardenable material using a resonator comprising detector elements embedded in the material, in which the resonator circuit is driven by a predetermined frequency which is known to differ from the resonant frequency of the resonator. The drive signal is applied to the resonator to allow the taking of a reading dependent on the impedance of the resonator at the predetermined frequency.

The resonant frequency of the resonator will depend on the characteristics of the surrounding material, which influence the complex impedance of the resonator circuit. The drive signal is influenced in a measurable manner dependent upon the resonator impedance. The non-linearity of the frequency response curve of the resonator means that relatively small changes in material characteristics can produce a significant difference in the measured effect of the impedance on the drive signal.

Preferably, the measurement technique involves taking two readings, one of them a measurement reading influenced by the characteristics of the resonator, and the other being a reference reading taken with the resonator switched out of circuit and indicative of the power level (e.g. the amplitude) of the drive signal. Both readings are used to derive a material characteristic measurement value. This reduces the influence of component tolerances, measurement conditions, etc. on the resulting derived value. Instead of requiring a power-level reading, with sufficiently close-tolerance components it may be possible to generate drive signals of predetermined power without the need for reference measurements.

In a more preferred arrangement, the measurement-taking technique involves taking two measurements of the influence of the resonator on the drive signal, each measurement being taken when the drive signal has a respective different power level. The derived output value is dependent upon the relationship between these two measurements. It has been found that such an arrangement can significantly reduce the variability of the output value.

In a technique according to a preferred embodiment of the invention, measurements are taken at multiple different predetermined frequencies, rather than a single frequency. All the frequencies are selected to lie on one side (i.e. above or below) of the resonant frequency, and the measurements are then combined (e.g. by summing or averaging). By spreading the measurements over a band of frequencies it is possible to mitigate the effect of erroneous measurements due to interference at a particular frequency, and it becomes easier to meet regulatory requirements regarding emission characteristics.

Although each of the aspects mentioned above is independently advantageous and can be used separately, certain additional advantages can be achieved by combining some or all of these aspects.

BRIEF DESCRIPTION OF THE DRAWINGS

An arrangement embodying the invention will now be described by way of example with reference to the accompanying drawings.

DETAILED DESCRIPTION OF THE PREFERRED EMBODIMENTS

Figure 2:
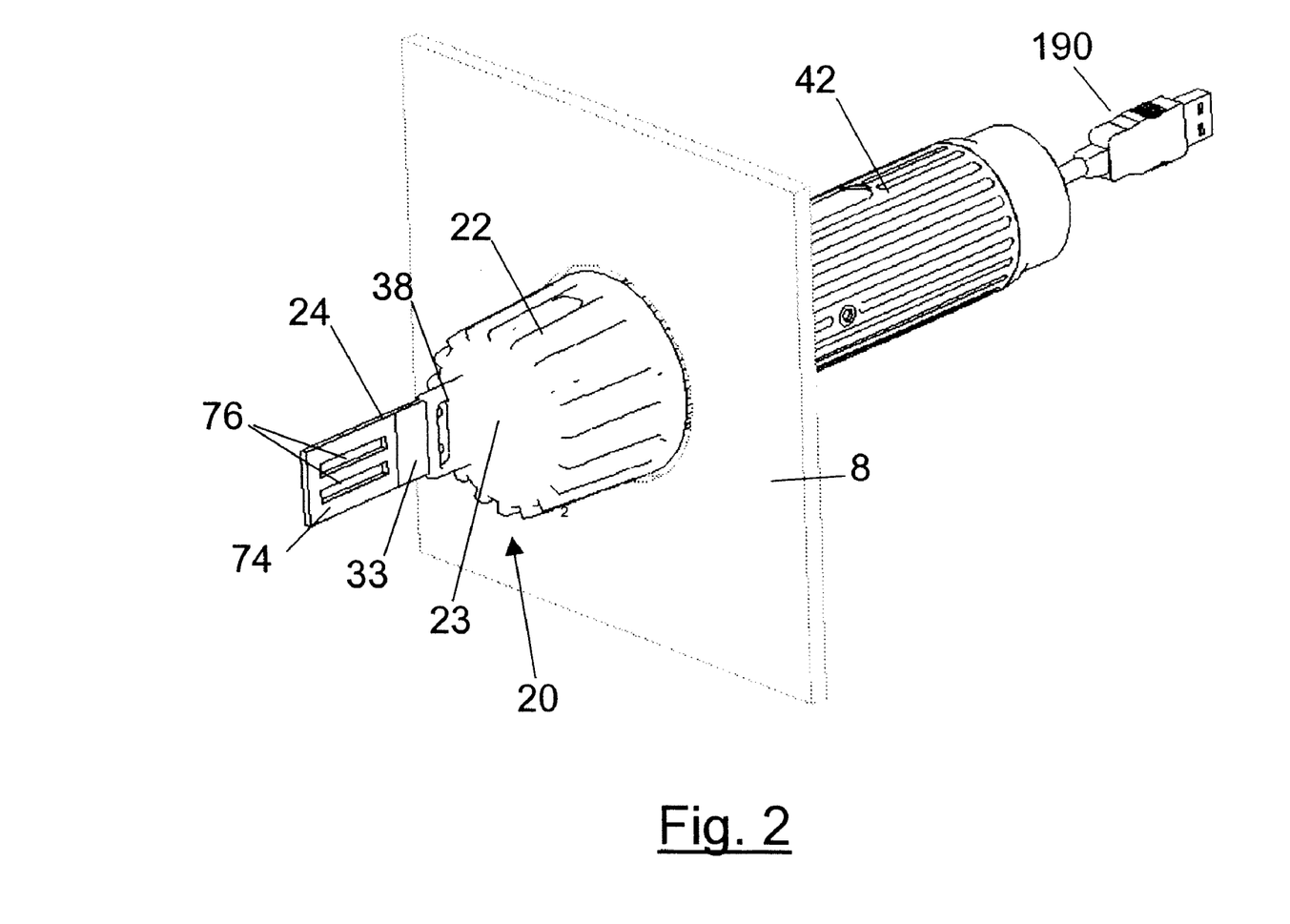
FIG. 2 is a perspective view of a measurement probe according to the present invention, supported on formwork and coupled to a measurement instrument.
Figure 3:
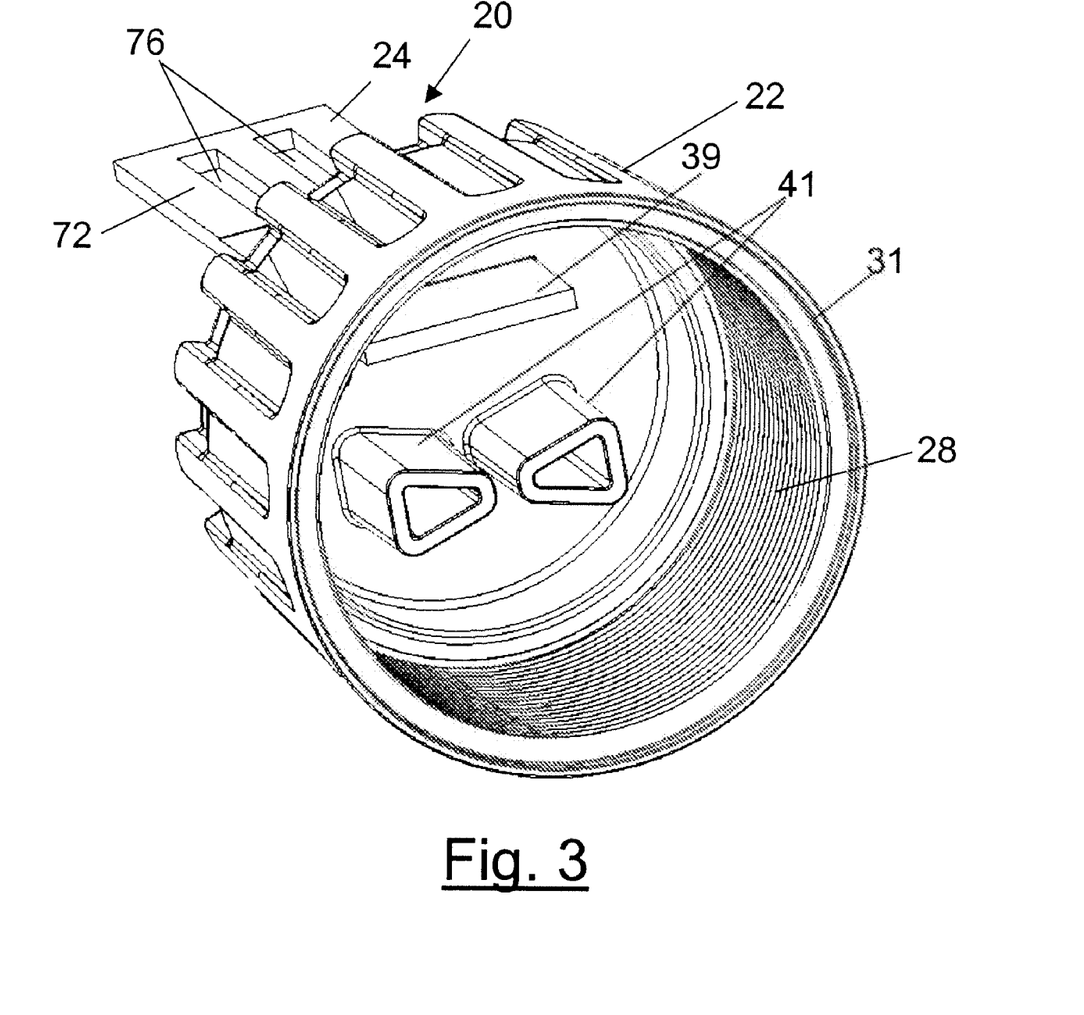
FIG. 3 is a further perspective view, showing the measurement probe from the proximal end thereof.
Figure 4:
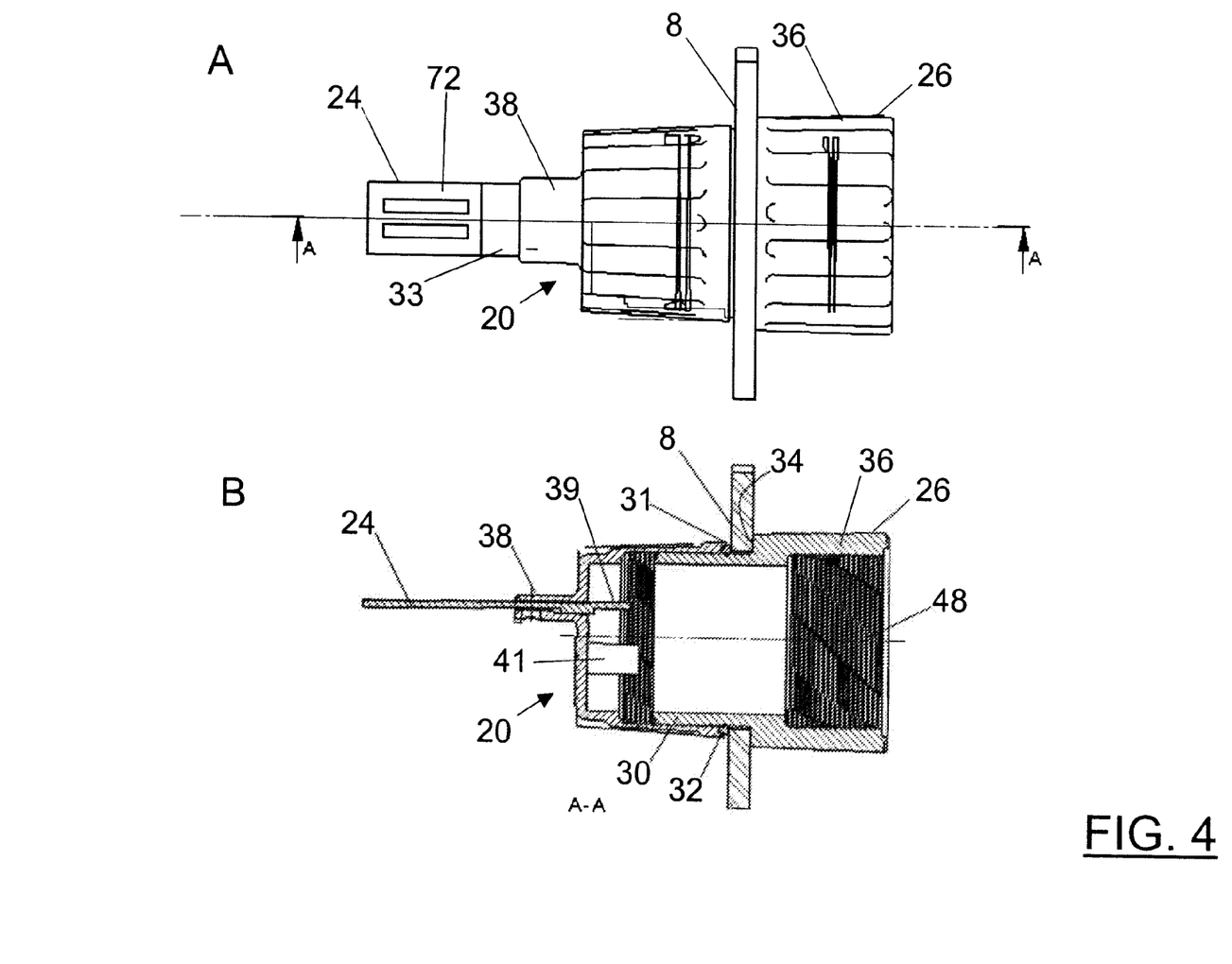
FIG. 4 comprises FIGS. 4A and 4B, which are respectively a side elevation of the probe and a retainer attached thereto, and a cross section through line A-A of the side elevation.

Referring to FIGS. 2 to 4, a measurement probe 20 comprises a hollow, generally cylindrical cup-shaped body 22 which is open at its proximal end and which has a closed, distal end 23 from which a sensor device 24 projects.

The probe 20 is intended to be embedded into concrete and can be supported in a number of different ways (as will be described below). In the mode of operation shown in FIGS. 2 and 4, the probe 20 is held on the inside of a mould wall formed by formwork 8, using a retainer 26 mounted on the outside of the formwork 8, but extending through an aperture in the formwork into the body 22 of the probe 20.

In the illustrated preferred embodiment, the body 22 of the probe 20 has a threaded inner cylindrical surface 28, for cooperating with the threaded outer cylindrical surface of an extension 30 of the retainer 26. At the proximal end of the cylindrical surface 28, the inner surface has a enlarged-diameter portion forming a recess surrounded by a lip 31 for accommodating a resilient O-ring 32 (see FIG. 4B).

The probe is mounted by fitting the O-ring 32 into its proximal end, holding the proximal end against a hole formed in the formwork 8 and then inserting the extension 30 of the retainer 26 through the hole and screwing it into the body 22 of the probe 20. The threaded extension 30 of the retainer 26 ends in a shoulder 34 of an enlarged portion 36 of the retainer 26. When the retainer 26 has been fully screwed into position, the assembly comprising the retainer 26 and the probe 20 is held firmly in position within the hole in the formwork, with the shoulder 34 abutting an annular region around the hole on the outside of the formwork 8 and the proximal end of the body 22 engaging an annular region around the hole on the inside of the formwork.

Concrete can then be poured into the formwork in order to embed the probe 20. Although significant internal pressures can be created, particularly if the probe 20 is mounted at the bottom of a large volume of concrete, the sealing ring 32 effectively prevents egress of the material through the hole in the formwork 8. Also, after removal of the formwork 8, the lip 31 will be disposed beneath the level of the surface of the concrete, so that the probe is completely submerged, as is often desirable.

The extension 30 of the retainer 26 and the threaded inner cylindrical bore 28 of the probe 20 extend over substantially large axial distances so as to accommodate formwork 8 of a large range of wall thicknesses. Other retainers 26, of different dimensions, could be provided if desired to accommodate still further thicknesses.

The sensor device 24 comprises a printed circuit board 33 which is held by a support formation 38 formed by moulded parts of the base 23 of the body 22 of the probe 20. The printed circuit board 33 extends inwardly of the base and has conductive portions (not shown) formed at a proximal end 39 to constitute terminals of the sensor device 24. The board also supports circuit components (not shown) as will be described in more detail below. The base 23 of the body 20 has, on the interior of the body, a locating structure 41 which extends proximally from the base 23 to a distance slightly greater than the end 39 of the printed circuit board.

A portable measurement instrument 42 (see also FIG. 5) can be fitted to the probe by inserting it through the retainer 26 and the body 22 of the probe. A locating recess 44 can be fitted on to locating projection 41 by twisting the generally-cylindrical measurement instrument 42 about its axis until the locating projection 41 interengages with the locating recess 44. (Obviously the projection and recess could instead be carried by the instrument 42 and probe 20, respectively.) Further axial movement of the measurement instrument towards the probe causes the proximal end 39 of the printed circuit board to be inserted into a circuit board connector 46 of the measurement instrument in order to connect terminals (not shown) of the measurement instrument to the terminals of the sensor device.

Figure 5:
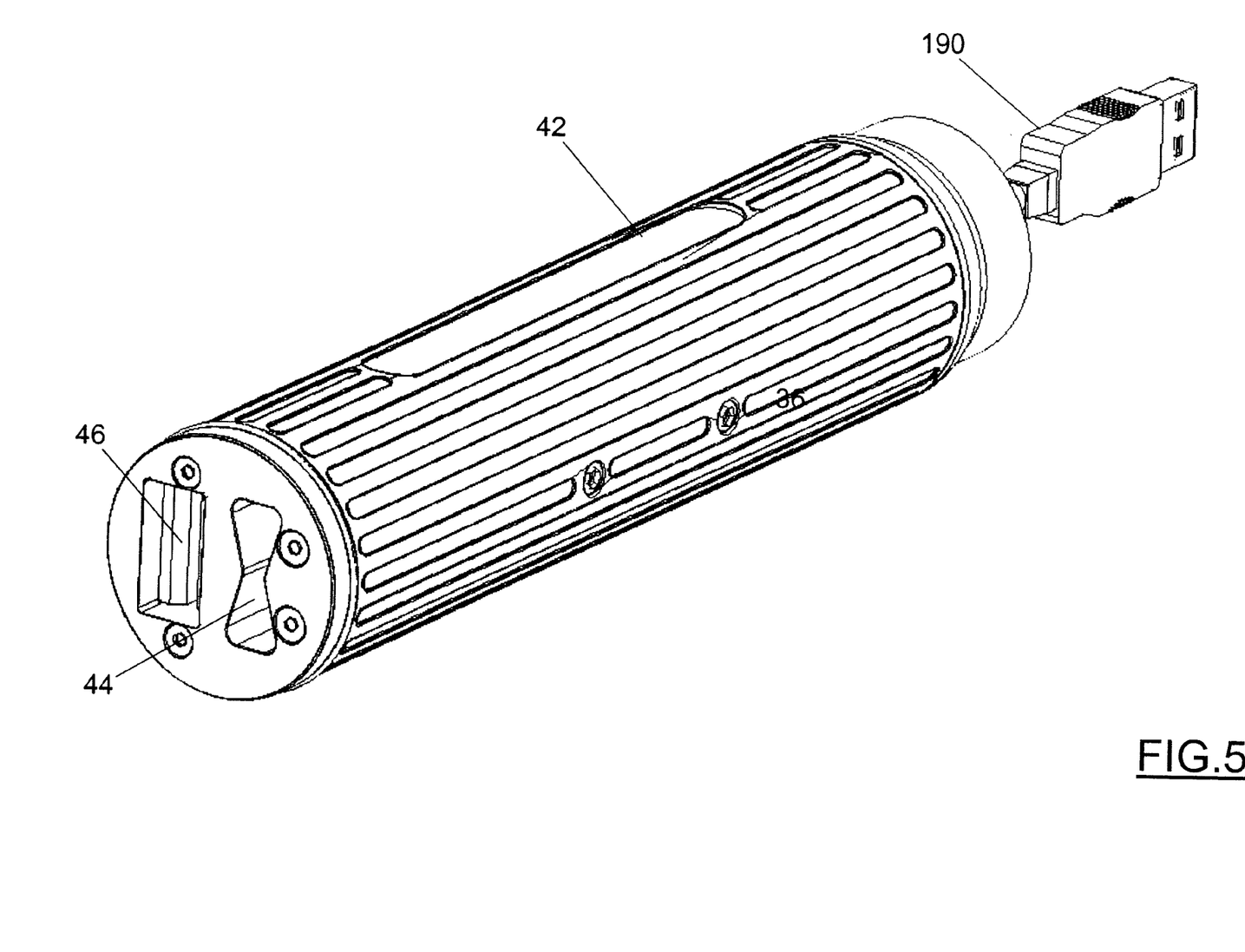
FIG. 5 is a perspective view of the measuring instrument of FIG. 2.

It is not always easy to access the outside of the formwork 8 at positions at which probes are mounted. If desired, the measurement instrument 42 may be mounted on the distal end of a tubular extension by means of which it can be held at a position relatively distant from the formwork but nevertheless inserted through the retainer 26 into cooperation with the probe. To aid this, the enlarged part 36 of the retainer 26 is preferably provided with an inner cylindrical threaded surface 48 by means of which a supporting tube can be threadably engaged with the retainer 26. The supporting tube thus guides the measurement instrument 42 as it is pushed towards and through the retainer 26.

The arrangement described above requires the probe 20 to be held on the inside of the formwork 8 in order to fix the probe into position. However, there may be circumstances in which there is no ready access to the interior of the formwork at the location where the probe is to be mounted. In this case, a different retainer, as shown in FIG. 6, is used.

Figure 6:
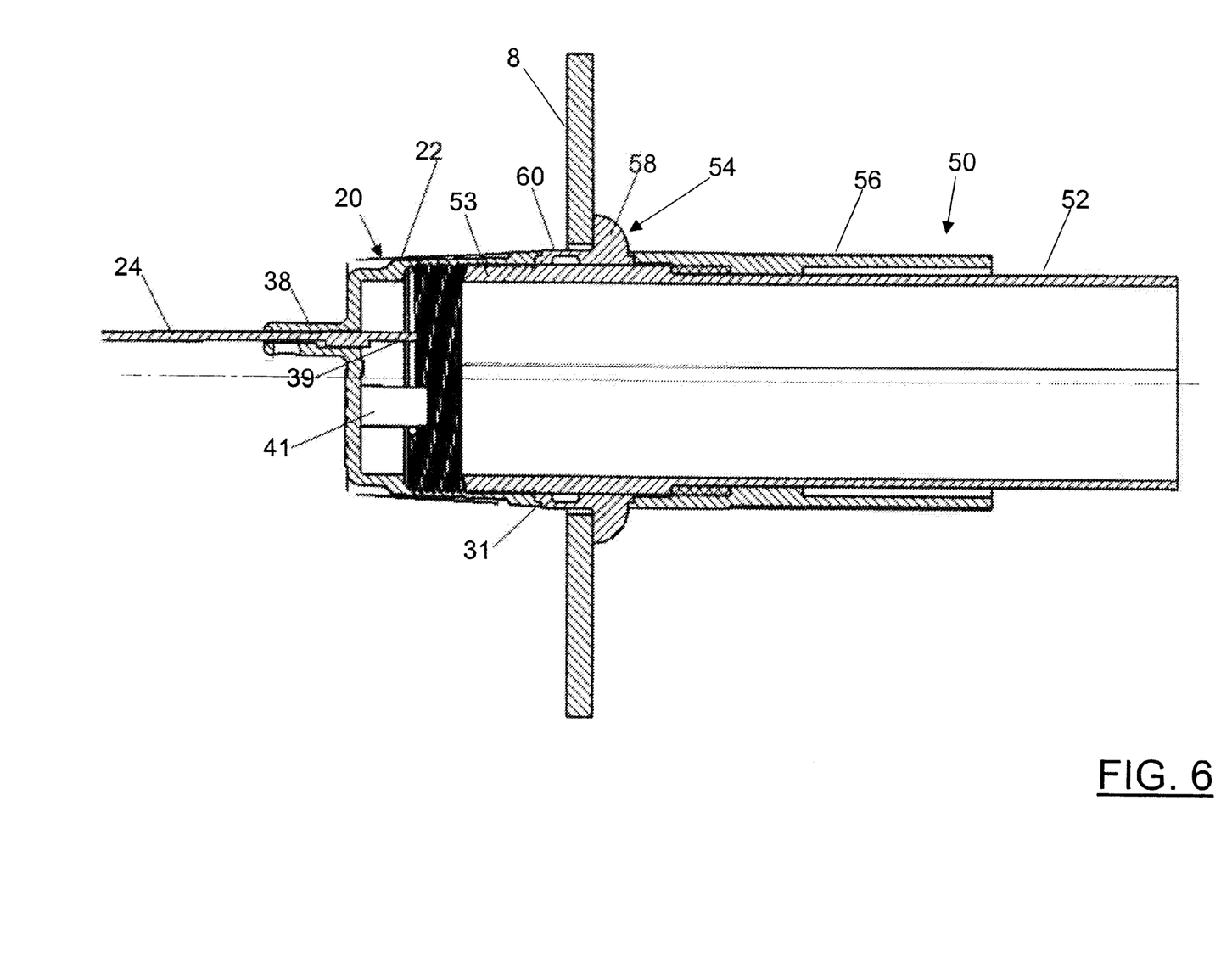
FIG. 6 is a cross section through the measurement probe and a different retainer.

In the arrangement of FIG. 6, the formwork 8 is provided with a hole which is sufficiently large that the probe 20 can pass through the hole. Prior to this, the probe is mounted on a retainer 50 having a main tubular portion 52 which is threaded on its outer distal end 53 for cooperation with the inner threaded surface 28 of the probe 20. The retainer 50 also carries an annular resilient member 54 around its distal end, and a locking sleeve 56 around the main body portion 52, and located proximally with respect to the member 54. The sleeve 56 has an inner threaded surface engaging an outer threaded surface of the main portion 52 of the retainer 50, so that rotation of the sleeve 56 with respect to the main body portion 52 causes the sleeve 56 and body 52 to move axially relative to each other.

The annular member 54 has an enlarged-diameter portion 58 with an outer diameter larger than the diameter of the hole in the formwork 8. The member 54 also has a small diameter portion 60 which extends axially from the enlarged diameter portion 58 towards the distal end of the retainer 50. As shown more clearly in FIG. 7, the distal end of the small diameter portion 60 has a reduced diameter annular projection 62 which locates under the lip 31 of the probe body 22, which in the arrangement of FIG. 4 accommodates the O-ring 32. An intermediate portion of the small-diameter extension 60 has an enlarged inner circumference to form a thin wall 64.

Figure 7:
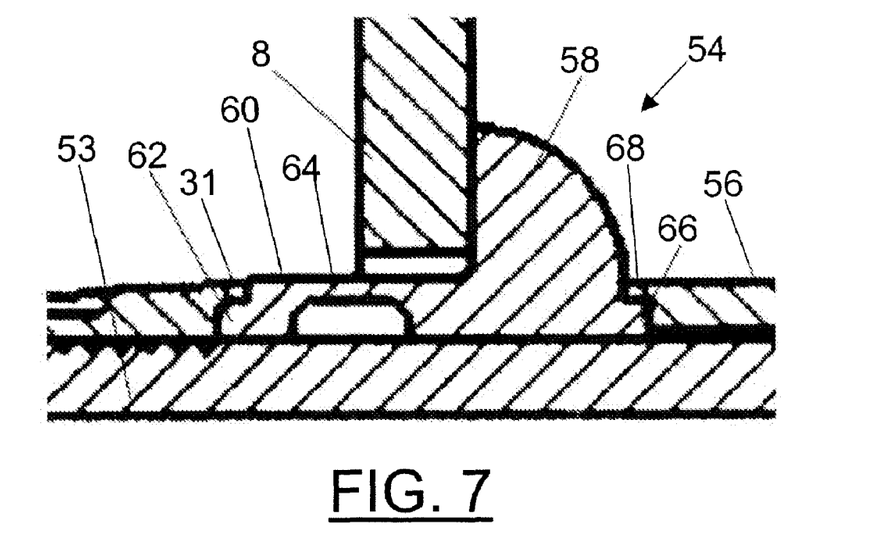
FIG. 7 is an enlarged view of part of the measurement probe and retainer shown in FIG. 6.

In operation, the distal end of the retainer 50 with the probe 20 attached thereto is inserted through the hole in the formwork 8 until the enlarged portion 58 of the member 54 engages the formwork. The sleeve 56 is then rotated relative to the main body 52 so that the member 54 is compressed between the sleeve 56 and the probe body 22. The compressive forces applied to the small diameter extension 60 of the member 54 will cause the extension 60 to buckle outwardly in the area of the thin wall 64 so that the inner circumference of the hole in the formwork 8 is gripped by the outward expansion of the extension 60. The retainer 50 and attached probe 20 are thus firmly held in position in the hole. The engagement of the annular projection 62 under the lip 31 of the body 22 ensures that the member 54 does not slip over the outside of the body 22 during this operation. It will be noted also that the member 54 has a proximally-extending extension 66 located under a lip 68 of the sleeve 56, to ensure that the member 54 does not slip over the outside of the sleeve 56.

In this embodiment the annular member 54 used for holding the probe and retainer in position serves also the additional function of sealing the hole in the formwork 8.

The retainer can also be used to advantage when the interior of the formwork 8 is accessible. In this case, the orientation of the member 54 may be reversed, so that the enlarged diameter portion 54 is on the inside of the formwork 8. This provides an even more effective seal against egress of concrete through the hole in the formwork.

It will be appreciated that the frictional engagement of the member 54 with, on the one hand, the sleeve 56 and, on the other hand, the probe body 22 could cause the rotational forces applied to the sleeve 56 to be transmitted to the body 22. It is desirable to prevent the possibility that this will cause the body 22 to be unscrewed from the end of the retainer 50. Accordingly, it is preferred that the cooperating threads on the inner surface 28 of the body 22 and the outer cylindrical surface of the main retainer portion 52 be threaded in the opposite sense from the cooperating threads on the inner cylindrical surface of the sleeve 56 and the outer cylindrical surface of the main retainer portion 52. For example, the former cooperating threads may be right-hand threads, and the latter left-hand threads. Accordingly, any rotational movement transmitted from the sleeve 56 as the sleeve tightens against the member 54 would, if transmitted to the body 22, cause additional tightening of the body on to the end of the retainer 50.

The retainers mentioned above, and the probe body, may for example be made from moulded plastics material or rubber.

The sensor device 24 of the probe 20 includes a resonator formed by a conductive portion 72 on one side of the printed circuit board at its distal end and a conductive portion 74 on the other side (see FIGS. 2 to 4). In this embodiment, the portions are of the same shape and extend over the same area. Two elongate gaps 76 extend through the printed circuit board to permit more intimate contact of the concrete with the resonator element, and to extend the regions adjacent edges of the conductive portions. It is desirable to use gaps dimensioned to have a significant effect; for example the gaps should preferably occupy an area not less than 10% of the area bounded by the outer edges of the detector elements.

Each conductive portion 72, 74 is connected via conductive traces on the printed circuit board to a respective terminal at the proximal end 39 of the printed circuit board. The circuit board also carries additional components connected to the terminals, these components being mounted on the portion of the printed circuit board held by the supporting structure 38. This portion and the supporting structure may be sealed, for example using heat shrinkable plastics material or resin.

Figure 8:
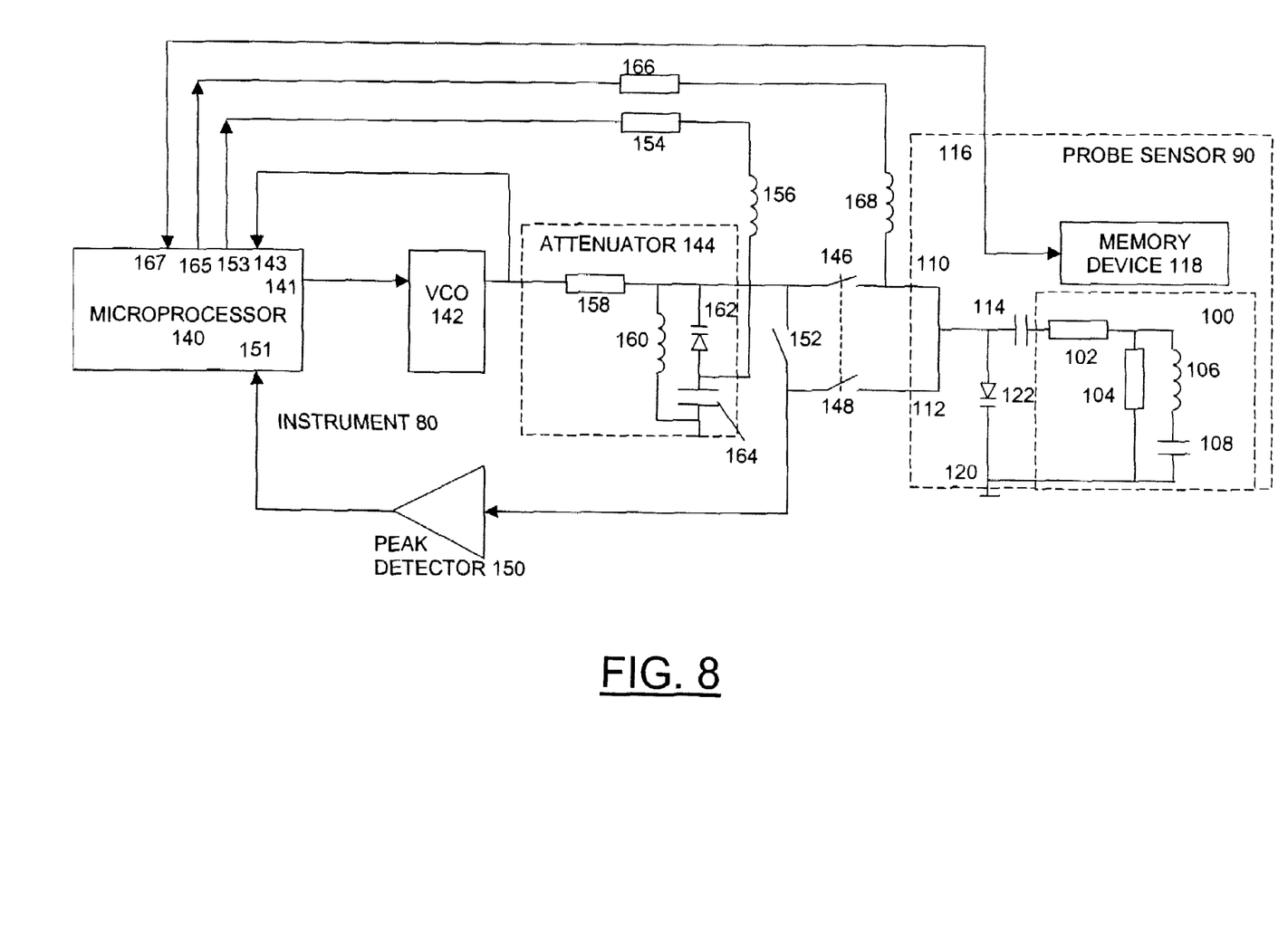
FIG. 8 schematically shows the circuit of the measurement instrument and measurement probe.

FIG. 8 is a schematic circuit diagram of the measurement instrument 80 and the sensor circuit 90, the resonator forming part of the sensor circuit 90 having an equivalent circuit as shown at 100. The equivalent circuit comprises a pair of resistors 102, 104 in series, with a series-connected inductance 106 and capacitance 108 connected across the resistor 104, thus forming a resonant circuit. The various component values of the equivalent circuit will vary depending upon the characteristics of the material surrounding the resonator.

The terminals of the sensor circuit include a power supply terminal (not shown), and a pair of input/output terminals 110, 112 connected to the resonator 100 by a series capacitor 114, although only a single input/output terminal could be used, if desired. There are also provided one or more further terminals 116 connected to a memory device 118 supported by the printed circuit board, and one or more ground terminals 120.

The sensor circuit 90 also includes a PIN diode 122 connected between the input/output terminals 110, 112 and the ground terminal 120. The PIN diode 122 can be operated to function as a switch, effectively shorting out the resonator 100.

The sensor circuit 80 comprises a microprocessor 140 controlling measurement operations. One output 141 of the microprocessor controls the frequency at which a voltage controlled oscillator (VCO) 142 operates. The output of the VCO 142 is delivered to a microprocessor input terminal 143, and, via an adjustable attenuator 144 and a switch 146, to the input terminal 110 of the sensor device 90. This enables a drive signal of predetermined frequency and amplitude to be applied via the capacitor 114 to the resonator 100. The resonator will influence the amplitude of the drive signal. This can be sensed via the output terminal 112, which is coupled via a switch 148 to the input of a peak detector (or envelope detector) 150. The output of the peak detector 150 is delivered to an input 151 of the microprocessor 140, which has internal circuits for determining the amplitude of the signal input thereto.

With the switches 146 and 148 open, the output of the attenuator 144 can be presented, by closing a switch 152, to the input of the peak detector 150. In this way, the sensor circuit 90 can be disconnected and a reference measurement made by the microprocessor 140.

The microprocessor controls the switches 146, 148 and 152 using control signals (not shown) in a manner well known per se. The microprocessor can also deliver a variable amplitude signal from output 153 via a resistor 154 and an inductance 156 to the attenuator 144, in order to control the level of the signal at the output of the attenuator. The attenuator comprises a series resistor 158, the output of which is connected to ground via a circuit comprising a inductor 160 in parallel with a series-connected PIN diode and capacitance 162 and 164, respectively. The conductivity of the PIN diode 162 is controlled by the DC level of the signal received from the microprocessor via the resistor 154 and inductor 156, which is coupled to the junction between the PIN diode 162 and the capacitor 164. The inductor 156 blocks the high frequency output of the VCO, so as to avoid influencing the high-frequency measurements made using the peak detector 150.

The microprocessor can also, using an output terminal 165, apply a DC voltage via a resistor 166 and an inductance 168 to the input terminal 110 and thus the PIN diode 122. This causes the PIN diode 122 to form an effective short between the input terminal 110 and the ground terminal 120. The inductance 168 prevents this arrangement from having any significant effect on the high frequency signal received by the peak detector 150.

The microprocessor also has one or more input/output terminals 167 connected to the sensor terminal(s) 116 and thus the memory device 118 to permit data to be read from and/or written to the memory device 118.

Figure 9:
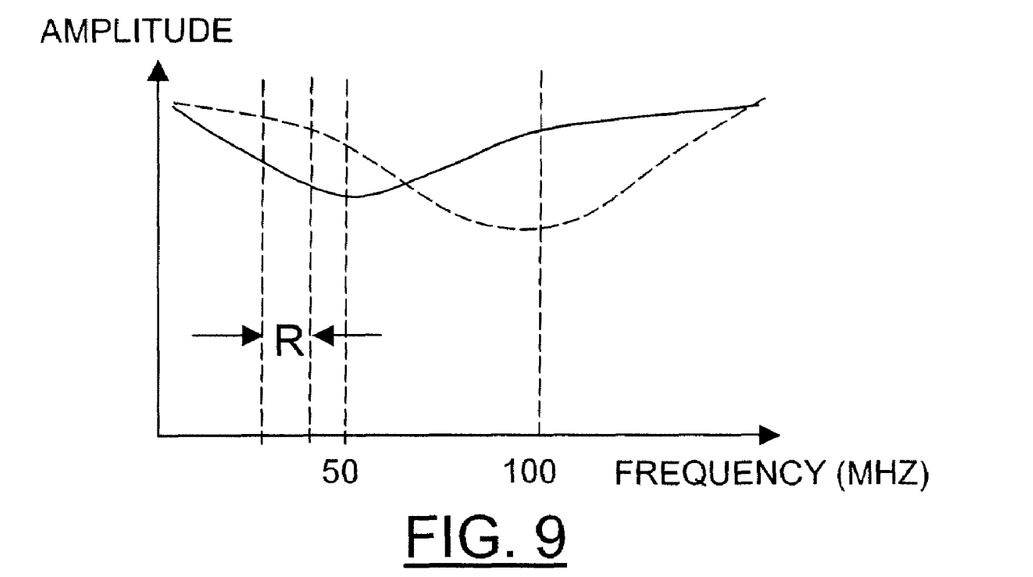
FIG. 9 is a graph illustrating the response characteristics of the measurement probe.

The operation of the circuit will be described below. First, however, reference is directed to FIG. 9, which is a graph illustrating the effect of frequency on the amplitude of the drive signal as measured using the peak detector 150. The broken line shows the amplitude/frequency response curve for the sensor circuit when the resonator is surrounded by air. It will be seen that the minimum level of the amplitude (which occurs when the impedance of the resonator is at its minimum value) is at approximately 100 MHz corresponding to the resonant frequency of the resonator in those conditions. However, in wet concrete, the resonant frequency decreases to around 50 MHz. Because of the use of a resonator, there is a significant variation in amplitude with frequency. Furthermore, there is a significant change in the response curve depending upon the characteristics of the surrounding materials. Accordingly, there is a large difference between the amplitude values found, for example, in a range R of 28 to 40 MHz, as shown in FIG. 9, depending upon the material characteristics. Therefore, an indication of the material characteristics can be obtained by taking an amplitude measurement within this frequency range.

Apparatus of the present invention can be used to measure various characteristics, including the hydration state of the material, which is an important indicator of concrete hardness. The measurement of the amplitude of the drive signal within the frequency range R mentioned above would give an indication of the hydration state. The amplitude varies as a function of the strength of the signal applied thereto, but this variability can be taken into account by using a reference value corresponding to the strength of the signal. In practice, it is preferred to derive this value by measuring the output of the attenuator 144, although in theory, with sufficiently close-tolerance components, it would instead be possible for the microprocessor to control the attenuator to generate a predetermined output without such measurement.

However, the measurement would also be influenced by a number of other factors including component values, temperature, etc. It has, however, been found that although a given measurement could represent different hydration states, the extent to which the amplitude varies with respect to the strength of the signal applied to the resonant circuit is a relatively reliable indicator of the hydration state. Thus, it would be desirable to derive a characteristic-representing value measurement which depends on the relationship between the measured amplitude of the signal at different power levels.

As indicated above, it is desirable to take a reading at a frequency within, for example, the frequency range R indicated in FIG. 9. In a preferred embodiment of the invention, however, readings are taken at multiple different frequencies to derive a measurement value. In this way, it is not necessary to concentrate the power applied to the resonator at a particular frequency, thus rendering it easier to avoid problems due to regulatory emission requirements and also avoiding potential errors if particular frequencies are subject to interference or otherwise give anomalous results.

Taking into consideration the above factors, the measurement instrument of FIG. 8 is arranged to operate in the following way in order to (a) take into account the level of the applied drive signal when reading the effect of the resonator; (b) take multiple measurements at different frequencies; and (c) take (at least) two measurements for each frequency at different levels of the drive signal, in order to provide a reliable value indicative of characteristics of the construction material.

First, the microprocessor 140 is operable to ensure that the switch 152 is opened and that the switches 146 and 148 are closed. Then, the microprocessor applies a DC voltage to the PIN diode 122 via the resistor 166 and the inductor 168. At that point, a measurement is taken of the output of the peak detector 150. Because the DC voltage acts to drive the PIN diode 122 into conduction, the output of the attenuator 144 is effectively shorted. The capacitor 114 prevents the resonator 100 from adversely influencing this operation. Accordingly, the output of the peak detector 150 should be measured to be substantially zero (ground level). Assuming that the measured level differs significantly from that level, then it is determined that there may be a fault in the connections between the measurement instrument 80 and the sensor circuit 90, and the microprocessor generates an error signal.

Otherwise, the DC voltage is removed, to open the switch formed by the PIN diode 122. Then, the switches 146 and 148 are opened, and the switch 152 closed. The microprocessor controls the voltage controlled oscillator 142 to generate a first frequency, of for example 28 MHz. This can be achieved by measuring the frequency of the oscillator at input 143 and varying the voltage at output terminal 141 until the correct frequency is obtained. The output of the attenuator is measured using the peak detector 150, and varied by altering the voltage applied to the attenuator 144 via the resistor 154 and inductor 156 until the attenuator output reaches a first predetermined voltage.

At that time, the switch 152 is opened and the switches 146 and 148 are closed. This will cause a drive signal of the predetermined voltage and the desired frequency to be applied via the input terminal 110 and the capacitor 114 to the resonator 100. The resonator 100 will influence the amplitude of the drive signal to an extent dependent on the characteristics of the surrounding material. The output voltage is presented via output terminal 112 and switch 148 to the input of the peak detector 150, and is thereby measured by the microprocessor 140.

This operation is repeated after controlling the VCO to adopt a second frequency, thereby obtaining a second measurement with the attenuator output set to the first predetermined level. The operation continues until 32 measurements have been made, each measurement being made at a respective different frequency within the range 28 to 40 MHz.

These measurements are then combined. In the preferred embodiment, this is achieved by summing the measurements, although other techniques could be used. For example, a weighted sum could be used, with higher-frequencies being given a greater weight, in view of the fact that (as shown in FIG. 9) frequencies closer to the resonant frequency exhibit bigger changes as a result of changes in material characteristics.

The microprocessor then opens the switches 146 and 148 and closes the switch 152, and thereafter controls the voltage control oscillator 142 and the attenuator 144 until the output of the oscillator adopts the first predetermined frequency again, and the output of the attenuator adopts a second predetermined level which is greater than the first predetermined level. The operation proceeds as above in order to derive 32 more measurements, at the higher output level of the attenuator, these measurements then being combined as before.

Accordingly, at the end of this operation, the microprocessor derives two material measurements, M1 and M2, each formed by combining 32 individual measurements at different frequencies, and each corresponding to a respective different reference level R1 and R2.

The microprocessor then derives an output value $V=(M1-M2)/(R1-R2)$. If desired, an additional temperature compensation factor can be applied to the resulting value.

The output value is representative of characteristics related to the hardness of the material in which the probe is embedded. These readings can be repeated whenever desired, for example to determine when the formwork 8 can be removed, and/or to predict the ultimate strength of the concrete.

The measurements may be output via a port, for example using a USB cable and plug 190 (see FIGS. 2 and 5). Additionally, the measurements could be stored in the memory device 118 carried by the probe 20. The memory device 118 may also or alternatively store a unique identification number associated with the probe.

Various changes can be made to the arrangement described above. For example, although the preferred embodiment takes readings at two different levels of the attenuator, more than two levels could be used if desired. The level of the attenuator could be adjusted each time the frequency is changed. The multiple frequencies could instead be applied concurrently, so separate readings of different frequencies are not needed. Instead of using multiple frequencies, a single frequency could be used. The frequency or frequencies used for measurement could be all located either below or above the range of resonant frequencies likely to be encountered in practice.

Different measurement techniques could be used. For example, the attenuator could be a constant current source or sink capable of operation at different current levels, under the control of the microprocessor. Alternatively, the attenuator could be replaced by a circuit which is adjusted, with the resonator 100 in circuit, until the voltage across the resonator reaches a predetermined level; in this case, a reading is taken either by detecting the level of current flowing through the resonator or by measuring the level of the control signal applied to the attenuator.

The switch formed by the PIN diode 122 could additionally or alternatively be used in place of the switches 146, 148 and 152 for permitting reference readings to be taken while the resonator 100 is switched out of circuit.

In an embodiment, a probe for measuring a characteristic of hardenable construction material comprises a body adapted to receive a retainer such that the combined body and retainer can be held in an aperture extending through a wall of a mould for the hardenable material, with the body extending from the inside of the wall, and a sensor circuit comprising detector elements supported by the body and disposed, in use, in the material, and circuit terminals which, in use, face the exterior of the mould wall and are accessible through the retainer for connection to terminals of an external instrument. The detector elements may form a resonator. The body may be threaded for attachment to a threaded retainer. The body may be threaded on an inner cylindrical surface thereof.

In an embodiment, the probe is a component of a probe assembly which further comprises a retainer for cooperating with the body of the probe to support the probe on a mould wall. In one such embodiment, the retainer comprises: (i) a body portion for extending through the aperture and being received by the probe body; (ii) a sleeve surrounding the body portion; and (iii) a resilient member surrounding the body portion and located, in use, between the sleeve and the probe body, with at least a portion of the member extending through the aperture, wherein the sleeve can be moved with respect to the body portion to compress the resilient member between the sleeve and the probe body, thus expanding the diameter of the member within the aperture and causing the probe and retainer to be held in position in the aperture. In another such embodiment, the retainer includes first portion with a threaded outer cylindrical surface for extending through the aperture in the wall and threadedly engaging the threaded inner cylindrical surface of the probe body, and a second portion having a shoulder for bearing against the mould wall in a region around the aperture.

In another embodiment, a probe for measuring a characteristic of hardenable construction material comprises a resonator including detector elements which are, in use of the probe, embedded in the material, wherein the detector elements are formed by conductive portions of a printed circuit board. In this embodiment, the detector elements may comprise first and second elements disposed on respective sides of the printed circuit board. Also, in this embodiment, along at least one direction, the detector elements may be divided into a plurality of sub-regions with gaps therebetween, the gaps extending through the printed circuit board to permit the hardenable material to be received therein. The gaps may form elongate slots.

In another embodiment a probe for measuring a characteristic of hardenable construction material comprises a sensor circuit which includes detector elements disposed in use in the material, at least two circuit terminals connectable to terminals of an external instrument, and a switch connected between said terminals and closable by a signal from the external instrument so that correct coupling of the instrument terminals to the circuit terminals can be detected by the instrument. The switch may be closable by application of a DC voltage across the circuit terminals. Each of the terminals is connected to a respective one of the detector elements, at least one of the terminals being connected to a respective element via a capacitor. The detector elements may form a resonator.

In a method of measuring a characteristic of hardenable construction material using a resonator including detector elements embedded in the material, the method comprises generating a drive signal having a predetermined frequency different from the resonant frequency of the resonator, applying the drive signal to the resonator to allow the taking of a reading dependent on the impedance of the resonator at the predetermined frequency, and generating a material characteristic-indicating signal dependent on the reading. The method may also include generating a drive signal having different predetermined frequencies either all below or all above the resonant frequency of the resonator. the method may further include taking separate readings dependent on the impedance of the resonator at the predetermined frequencies, combining the readings and generating a characteristic-indicating signal dependent on the combined readings. The method may further involve using a reference value indicative of a level of the drive signal while the drive signal is not being applied to the resonator to derive the characteristic-indicating signal. The method may further comprise generating first and second drive signals of different levels, taking first and second readings dependent on the impedance of the resonator while the first and second drive signals are respectively applied thereto, and generating a characteristic-indicating signal dependent on the ratio of the difference between the first and second readings and the difference between first and second reference values indicative of the levels of the first and second drive signals, respectively.

Various techniques have been described for mounting the probe 20 into a mould wall, such as formwork used to cast concrete. In some circumstances, it may be desirable to measure the properties of the concrete at a top surface thereof. In that case, there may be no formwork in the required location. In that event, the probe 20 could be fixed below a large-area sheet of, for example, wood, which would float on the surface of the concrete to enable the probe to be held in the right location.

We claim:

1. A system for measuring a characteristic of hardenable construction material, the system comprising:
   a probe comprising a sensor circuit having:
      detector elements arranged to be disposed, in use, in the hardenable construction material;
      circuit terminals; and
      a memory device,
   a measurement instrument removably coupled to the probe and operative to read data from or write data to the memory device, the measurement instrument comprising:
      instrument terminals operative to couple with the circuit terminals of the probe; and
      a processor for controlling measurement operations,
   wherein the probe further comprises a body which is adapted to receive a retainer such that the combined body and retainer can be held in an aperture extending through a wall of a mould for the hardenable material, with the body extending from the inside of the wall, and wherein the detector elements of the sensor circuit are supported by the body for disposal, in use, in the hardenable material, and wherein the circuit terminals are arranged to face, in use, the exterior of the mould wall to be accessible through the retainer for connection to said instrument terminals.

2. The system as claimed in claim 1, wherein the measurement instrument is operative to generate a value representative of said characteristic of the hardenable material and to store said value representative of said characteristic of said hardenable material in the memory device.

3. The system as claimed in claim 1, wherein the sensor circuit further comprises a power source terminal.

4. The system as claimed in claim 1, wherein the body is threaded for attachment to a threaded retainer.

5. A system for measuring a characteristic of hardenable construction material, the system comprising:
   a probe comprising a sensor circuit having:
      detector elements arranged to be disposed, in use, in the hardenable construction material;
      circuit terminals; and
      a memory device,
   a measurement instrument removably coupled to the probe and operative to read data from or write data to the memory device, the measurement instrument comprising:
      instrument terminals operative to couple with the circuit terminals of the probe; and
      a processor for controlling measurement operations,
   wherein the detector elements form part of an electromagnetic resonator, and the detector elements are formed by conductive portions of a printed circuit board.

6. The system as claimed in claim 5, wherein the detector elements comprise first and second elements disposed on respective sides of the printed circuit board.

7. The system as claimed in claim 5, wherein, along at least one direction, the detector elements are divided into a plurality of sub-regions with gaps therebetween, the gaps extending through the printed circuit board to permit the hardenable material to be received therein.

8. The system as claimed in claim 7, wherein the gaps form elongate slots.

9. The system as claimed in claim 8, wherein the sensor circuit further comprises a switch connected between said terminals and closable by a signal from the measurement instrument so that correct coupling of the instrument terminals to the circuit terminals can be detected by the measurement instrument.

10. The system as claimed in claim 9, wherein the switch is closable by application of a DC voltage across the circuit terminals.

11. The system as claimed in claim 9, wherein the circuit terminals comprise a pair of input/output terminals connected to respective ones of the detector elements, at least one of the input/output terminals being connected to a respective detector element via a capacitor.

12. A system for measuring a characteristic of hardenable construction material, the system comprising:
   a probe comprising a sensor circuit having:
      detector elements arranged to be disposed, in use, in the hardenable construction material;
      circuit terminals; and
      a memory device,
   a measurement instrument removably coupled to the probe and operative to read data from or write data to the memory device, the measurement instrument comprising:
      instrument terminals operative to couple with the circuit terminals of the probe; and
      a processor for controlling measurement operations,
   wherein the detector elements form an electromagnetic resonator.

* * * * *